United States Patent [19]

Sweger et al.

[11] Patent Number: 5,482,704
[45] Date of Patent: Jan. 9, 1996

[54] COSMETIC COMPOSITIONS CONTAINING AMINO-MULTICARBOXYLATE MODIFIED STARCH

[75] Inventors: Robert W. Sweger, Bound Brook; John J. Tsai, Belle Mead; Joseph Pasapane, Morristown, all of N.J.; Karen A. Bernard, Gaithersburg, Md.

[73] Assignee: National Starch and Chemical Investment Holding Corporation, Wilmington, Del.

[21] Appl. No.: 267,984

[22] Filed: Jun. 28, 1994

[51] Int. Cl.$^6$ ............................. A61K 7/06; A61K 7/48
[52] U.S. Cl. .................. 424/70.13; 424/59; 424/401; 514/60; 514/844; 514/847
[58] Field of Search .................... 424/401, 70.1, 424/70.13, 59; 514/60, 844, 847

[56] References Cited

U.S. PATENT DOCUMENTS

| | | | |
|---|---|---|---|
| 3,459,632 | 8/1969 | Caldwell et al. | 162/175 |
| 3,751,422 | 8/1973 | Bowden | 260/296 D |
| 4,017,460 | 4/1977 | Tessler | 536/50 |
| 4,119,487 | 10/1978 | Tessler | 162/175 |
| 4,260,738 | 4/1981 | Tessler | 536/49 |
| 4,705,889 | 10/1987 | Hendricks et al. | 562/564 |
| 5,256,404 | 10/1993 | Martino et al. | 424/59 |

FOREIGN PATENT DOCUMENTS

| | | |
|---|---|---|
| 496843 | 8/1992 | European Pat. Off. . |
| 45018217 | 6/1960 | Japan . |
| 57185208 | 11/1982 | Japan . |
| 58099407 | 6/1983 | Japan . |
| 61063608 | 4/1986 | Japan . |
| 4025502 | 1/1992 | Japan . |
| 1712503 | 1/1990 | U.S.S.R. . |

OTHER PUBLICATIONS

R. L. Whistler et al., *Starch: Chemistry and Technology*, Second Edition, 1984, pp. 332–364.
D. R. Howton, *J. Amer. Chem. Soc.*, "1,3–Diemthylpiperidone–4", 1945, pp. 277–282.
S. I. Suminov et al., *Russian Chem. Rev.*, "Nucleophilic Addition of Amino–groups to an Activated Carbon–Carbon Double Bond", 38 (11), 1969, pp. 884–899.

*Primary Examiner*—Jyothsna Venkat
*Attorney, Agent, or Firm*—Eugene Zagarella, Jr.

[57] ABSTRACT

Cosmetic skin and hair care compositions are provided containing amino-multicarboxylate starch derivatives as thickeners or emulsion stabilizers and which have the following formulas:

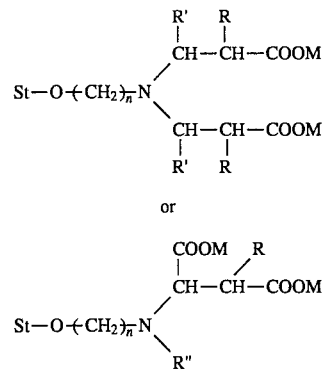

wherein
St-O represents a starch molecule;
R is H or $CH_3$;
R' is H, $CH_3$ or COOH;
M is a cation;
n is 2 or 3; and
R" is H or alkyl of 1 to 18 carbon atoms. These compositions have good rheological properties and have excellent aesthetic properties of feel and appearance.

16 Claims, No Drawings

COSMETIC COMPOSITIONS CONTAINING AMINO-MULTICARBOXYLATE MODIFIED STARCH

BACKGROUND OF THE INVENTION

This invention relates to cosmetic compositions for the treatment of skin and hair comprising amino-multicarboxylate starch derivatives as a thickener and emulsion stabilizer.

Various materials have been used to thicken and emulsion stabilize different cosmetic or personal care products. These materials include anionic derivatives of starch, xanthan gum and cellulose such as carboxymethylated starch or cellulose and phosphorylated starch and cellulose. Currently, Carbopol® resins, which are polyacrylic acid polymers produced by B. F. Goodrich, are the leading thickeners and emulsion stabilizers in the skin care and hair care markets.

Besides possessing the necessary rheological properties, the cosmetic product with the added thickeners and emulsion stabilizers must also have suitable appearance and feeling on the skin. The starch derivatives of this invention are natural materials and in addition to the thickening and emulsion stabilizing properties, they provide cosmetic formulations with excellent aesthetic properties of skin feel and appearance.

SUMMARY OF THE INVENTION

This invention is directed to cosmetic compositions which contain amino-multicarboxylate starch derivatives to provide thickening and emulsion stabilization and exhibit good appearance and feel to the skin.

More particularly, this invention relates to cosmetic compositions which contain an effective emulsion stabilization or thickening amount of amino-multicarboxylate starch derivatives having the following structure:

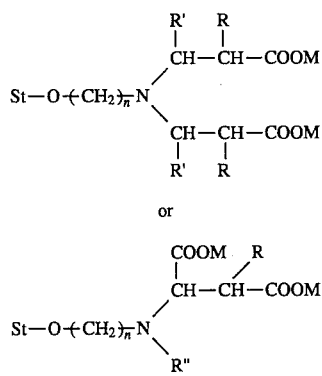

wherein

St-O represents a starch molecule or a modified starch molecule (wherein the hydrogen of a hydroxyl group of an anhydroglucose unit has been replaced as shown);

R is H or $CH_3$;

R' is H, $CH_3$ OF COOH;

M is a cation, more particularly H, alkali metal, alkaline earth metal or ammonium;

n is 2 or 3; and

R" is H or alkyl of 1 to 18 carbon atoms.

DETAILED DESCRIPTION OF THE INVENTION

The starch derivatives (I) and (Ia) used in the cosmetic compositions of this invention are made by reacting starch with selected amino-multicarboxylic acid reagents having the following formula:

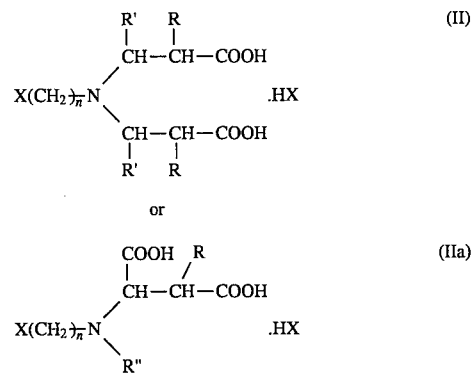

where

X is halogen;

R is H or $CH_3$;

R' is H, $CH_3$ or COOH;

n is 2 or 3; and

R" is H or alkyl of 1 to 18 carbon atoms.

The reagents (II) and (IIa) as defined above are provided by a Michael reaction between an aminoalcohol and a selected ester containing an activated olefin followed by halogenation.

The aminoalcohol used in preparing these reagents will generally have the formula

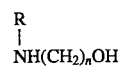

where R is H or alkyl of 1 to 18, preferably 1 to 8 carbon atoms, n is 2 or 3, and the olefin containing ester will be any such ester, for example, alkyl acrylates, alkyl methacrylates or alkyl crotonates and more particularly will have the formula:

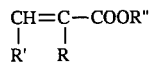

where R is H or $CH_3$, R' is H or $CH_3$ and R" is alkyl, and more particular, methyl, ethyl or propyl. Diesters of olefin containing esters, e.g., dialkyl maleates may be used to prepare the multicarboxylic acid reagents, particularly when the noted aminoalcohol has an alkyl R group.

The formation of the multicarboxylate starch derivative (I) or (Ia) involves reacting the selected multicarboxylate reagent (II) or (IIa) with a starch base in an aqueous medium using either an aqueous slurry or an aqueous dispersion of the starch base. The reaction is carried out under alkaline conditions at a pH of from about 9.5 to 13, more particularly from about 10.5 to 12.5. The pH is conveniently controlled by the periodic addition of a dilute aqueous solution of sodium hydroxide or other common base including potassium hydroxide, calcium hydroxide, sodium carbonate, ammonium hydroxide, tetramethylammonium hydroxide, etc. The preferred bases are sodium and calcium hydroxide.

The reaction is carried out at a temperature of from about 10° to 95° C., preferably from about 20° to 50° C. It will be recognized that the use of temperatures above about 60° C. with granular starches in an aqueous medium will result in granule swelling and filtration difficulties or gelatinization of the starch.

When conducting the reaction with granular starches, it may sometimes be desirable to carry out the reaction in the presence of salts, e.g., sodium sulfate, in amounts of from about 10 to 40% by weight, based on dry starch. The presence of sodium sulfate acts to suppress swelling of the starch and gives a more filterable product.

The amount of multicarboxylate reagent (II) or (IIa) to be employed in the reaction will vary from about 0.1 to 100% by weight, based on the weight of dry starch, and depending on such factors as the starch base used, the particular multicarboxylate reagent used, the degree of substitution required in the end product, and to some extent, the reaction conditions used. In general, the preferred amount of reagent to be used when preparing the starch ether derivative containing amino-multicarboxylate groups is about 0.3 to 15% by weight for granular starches and about 15 to 75% by weight for non-granular starches.

The multicarboxylate reagent may be added to the reaction mixture as a solid or an aqueous solution. The preferred concentration of the solution is 20 to 50% by weight, based on the weight of the reagent. In an alternative method, the carboxylate reagent solution is brought to the desired alkaline pH prior to its addition to the starch base. In this alternative method, the reagent is in the form of a salt rather than an acid or partially neutralized acid when it is introduced to the reaction mixture.

Reaction time will vary from about 0.2 to 24 hours depending on such factors as the amount, stability and reactivity of the multicarboxylate reagent employed, the temperature, pH, the scale of reaction and the degree of substitution desired. In general, the preferred range of reaction time is from about 1 to 16 hours.

After completion of the reaction, the pH of the reaction mixture is adjusted to from about 3 to 9 with any commercial acid such as hydrochloric acid, sulfuric acid, acetic acid, etc. Such acids may be conventionally added as a dilute aqueous solution. Depending on the final pH and the base used, the carboxyl group can be present as either the carboxylic acid, the corresponding salt or combination of the two (partially neutralized carboxyl groups). The cation M as found in starch derivatives (I) and (Ia) can be any cation and more particularly hydrogen, an alkali metal, an alkaline earth metal or ammonium. In the case of a multi-valent cation, e.g., calcium, the structure of the derivative could be cyclic.

Recovery of the resulting starch ether derivatives may be readily accomplished, with the particular method employed being dependent on the form of the starch base. Thus, a granular starch is recovered by filtration or centrifugation, optionally washed with water to remove any residual salts, and dried. The granular starch products may also be drum-dried, spray-dried, or gelatinized and isolated by alcohol precipitation or freeze drying to form non-granular products (i.e., gelatinized). If the starch product is non-granular, it may be purified by dialysis to remove residual salts and isolated by alcohol precipitation, freeze drying, or spray drying.

The applicable starch bases which may be used in preparing the starch ether derivatives herein may be derived from any plant source including corn, potato, sweet potato, wheat, rice, sago, tapioca, waxy maize, sorghum, oat, high amylose corn, or the like. Also included are the conversion products derived from any of the latter bases including, for example, dextrins, prepared by the hydrolysis of acid and/or heat; oxidized starches prepared by treatment with oxidants such as sodium hypochlorite; fluidity or thin-boiling starches prepared by enzyme conversion or mild acid hydrolysis; and derivatized starches such as ethers and esters. Starch esters will undergo hydrolysis when exposed to reaction conditions needed to prepare starch ethers. If mixed starch ethers/esters are desired, it is obvious to those skilled in the art that the ether substituents must be reacted first, followed by esterification. The intermediate starch ether can be directly esterified or isolated and purified prior to esterification. The starch base may be a granular starch or a gelatinized starch, i.e., non-granular starch.

The preferred starch derivatives (I) and (Ia) of this invention as described above, are those wherein R, R', and R" are hydrogen, M is hydrogen and n is 2 and more particularly those having the structure (I). The starch base is preferably potato starch. Also the starch base and the resulting starch derivatives may be further derivatized or modified with other groups such as cationic groups. Particularly useful cationic starches are the tertiary aminoalkyl starch ethers such as 2-diethylaminoethyl chloride and quaternary ammonium starch ethers such as 2,3-epoxypropyltrimethylammonium chloride.

The amino-multicarboxylate starch derivatives and the method of preparation are further described in copending application Ser. No. 08/190,824 filed Feb. 2, 1994, which is incorporated herein by reference.

The amino-multicarboxylate starch derivatives (I) and (Ia) are especially useful in cosmetic compositions such as skin care or hair care compositions where they provide thickening and emulsion stabilizing properties and other rheological and aesthetic properties. The skin and hair care compositions of this invention may involve different media or systems and will comprise a suitable cosmetic vehicle or base for the composition. This vehicle may be an emulsion, an aqueous system, a solvent system or a combination of aqueous and solvent systems.

The emulsions are the preferred vehicle or base for the cosmetic compositions of this invention and products of this type include the skin care creams and lotions. These emulsions which comprise water-based and oil-based phases, may be oil-in-water emulsions having oil as the dispersed phase and water as the continuous phase or they may be water-in-oil emulsions with water dispersed in oil, which is the continuous phase. The oil phase, which may comprise from about 10 to 90% by weight of the composition, is typically made up of cosmetically acceptable or conventional oily substances that are soluble in this phase, such as oils, waxes and emulsifiers. Compounds which can be included in the oil phase are typically mineral, animal and vegetable oils and fats, synthetic esters, fatty acids, aliphatic alcohols, higher fatty alcohols, alkyl amines, waxes, so called mineral fats and oils, such as paraffin oil, petrolatum, ceresin, silicone oils and silicone fats. The water phase may comprise from about 10 to 90% by weight of the composition and this will include water and water soluble components such as alkalis, alkanolamines, polyhydric alcohols and preservatives. These emulsions include one or more emulsifiers which usually are contained in the oil phase but in some instances, depending on the type, may be in the water phase. The starch derivatives (I) and (Ia) may be used to stabilize the emulsion or to replace secondary emulsifiers. Other emulsifiers which can be used may be ionic or nonionic are well known and constitute a large group of conventional and commercially available products. They are often characterized by their hydrophilic-lipophilic balance (HLB). Oil-in-water (O/W) emulsifying agents typically have an HLB of more than 6.0 and produce emulsions in which the continuous phase is hydrophilic and such emulsions are generally dispersible in water. Emulsifiers of this type include PEG 300 distearate, sorbitan monolaurate and triethanolamine stearate. Water-in-oil (W/O) emulsifiers usually have an HLB of less than 6.0, preferably below 5, and produce emulsions in which the continuous phase is lipophilic. Such emulsifiers include, lanolin alcohols, ethylene glycol monostearate, sorbitan mono-oleate and PEG 200 dilaurate. Emulsifiers with HLB's of between 5 and 7 may function as either W/O or O/W emulsifiers depending on how they are used.

The amount of emulsifier used in the emulsions of this invention including the starch derivatives (I) and (Ia) can vary depending on the system and typically will be an effective emulsifying amount. More particularly, the amount of emulsifier can vary from about 0.1 to 25% by weight of the composition and preferably from about 1 to 10%.

Various other ingredients and additives may be included in one or both of the oil and water phases in the cosmetic skin care emulsions described above. This includes emollients, humectants, thickening agents, UV-light inhibitors, preservatives, pigments, dyes, colorants, alpha hydroxy acids, aesthetic enhancers such as starch, perfumes and fragrances, film formers (water proofing agents) antiseptics, antifungal, antimicrobial and other medicaments and solvents. Effective amounts of one or more of these and other active and functional ingredients is generally used and this can total from about 0.1 to 25% by weight of the composition and more particularly from about 0.1 to 15%.

Other cosmetic compositions using the selected starch derivatives in accordance with this invention involve aqueous or solvent systems wherein the added components are soluble or dispersible therein. The aqueous system will comprise the selected starch derivatives, additives and active and functional ingredients, optionally a propellant and the balance water. Generally, an aqueous system will comprise from about 10 to 99.8% by weight water, preferably 50 to 80%, from about 0.1 to 20% by weight of the starch derivative, preferably 0.3 to 5%, from about 0.1 to 25% by weight of additives and ingredients, preferably 0.1 to 15% and from about 0 to 50% by weight of propellant, preferably 0 to 30%. Compositions of this type include the topical sprays and products containing fragrances and antimicrobial agents.

The topical sprays include the aerosol sprays or products containing a propellant. While any of the known propellants may be used in the compositions of this invention, preferred propellants included the non-halogenated hydrocarbons, particularly the lower boiling hydrocarbons such as $C_3$–$C_6$ straight and branched chain hydrocarbons, i.e., propane, butane, isobutane and mixtures thereof. Other preferred propellants include the ethers, such as dimethyl ether, hydrofluorocarbon and the compressed gases such as $N_2$ and $CO_2$.

The use of a solvent system as the vehicle or base involves other cosmetic compositions containing the selected starch derivative to provide thickening and/or emulsion stabilizing properties. The solvent system will comprise the selected starch derivative, additives and active and functional ingredients, optionally a propellant and the balance solvent. The solvent may be any of the known organic solvents which may solubilize or disperse components of the skin care composition and more particularly aliphatic alcohols, esters, ethers, ketones, amines and hydrocarbons including the aromatic, nitrated and chlorinated hydrocarbons. Particularly preferred organic solvents are the lower aliphatic alcohols such as the $C_{1-3}$ alcohols and especially ethanol. Generally the solvent system will comprise from about 25 to 99.8% by weight of solvent, preferably 50 to 80%, from about 0.1 to 20% by weight of the starch derivatives, preferably 0.3 to 5%, from about 0.1 to 25% by weight of additives and ingredients, preferably 0.1 to 15% and from about 0 to 75% by weight of propellant, preferably 0 to 35%.

The additives and other ingredients which may be included in either the aqueous or solvent based systems are the same as those described above for the emulsion and oil based systems. The propellants which may be included in the solvent system are the same as those described above for the aqueous systems. Additionally, a mixture of the aqueous and solvent systems may be used wherein water and solvent, especially alcohols are combined along with the components, i.e., starch derivative, additives and propellant. Such a composition will comprise 25 to 99.8% by weight of a combination of water and solvent, preferably 50 to 80% along with the components as described above.

The amino-multicarboxylate starch derivatives (I) and (Ia) used in cosmetic compositions in accordance with this invention will comprise an effective thickening or emulsion stabilizing amount. More particularly the amino-multicarboxylate starch derivative will comprise from about 0.1 to 20% and preferably from about 0.3 to 5% by weight of the cosmetic composition.

Preparation of the cosmetic emulsion compositions typically involves adding the oil soluble components in one vessel and heating to, e.g., 75° to 80° C. and combining the water soluble components in another vessel and heating to, e.g., 75° to 80° C. Depending on whether O/W or W/O emulsions are being prepared the warmed inner phase is then slowly added to the outer phase with agitation.

The following examples further illustrate the embodiments of this invention. In the examples all parts and percentages are given by weight and all temperatures in degrees Celsius unless otherwise noted.

EXAMPLE I

This example illustrates the preparation of starch modified with an amino-multicarboxylic acid reagent, i.e., 2-chloroethylaminodipropionic acid (hereinafter referred to as CEPA).

Overhead stirring was used throughout this reaction. Deionized water (150 mL) was added to a one liter beaker and heated to 45° C. with an external constant temperature bath. Sodium sulfate (30 g; 30% on starch) was dissolved in the water followed by the addition of potato starch (100 g) into the solution in portions to form a uniform slurry. A solution of 3% aqueous sodium hydroxide (25 mL) was added slowly with good agitation to minimize starch swelling. A 25% aqueous solution of CEPA reagent (32 mL) to give an 8% starch treatment (dry basis) was added simultaneously with a 3% aqueous sodium hydroxide solution (170 mL) at addition rates that kept the level of caustic high (pH of about 11.0 to 11.5) in the reaction. The reaction was run at 42° to 45° C. for 16 hours and then neutralized with addition of 3 N HCl to a pH of about 6.5 followed by stirring for 30 minutes. The starch was then filtered and washed two times with 150 mL of water and allowed to air dry. Analysis of the starch for bound nitrogen showed 0.25% N (dry basis) indicating that the starch had been modified with the aminodicarboxylic acid reagent (CEPA).

A 1% starch cook of the CEPA starch derivative prepared above was made (1 g of the derivative in 99 mL of deionized $H_2O$) for 20 minutes. The cook of the CEPA potato starch thickened within a minute and produced a translucent gel with a smooth consistency and an excellent non-tacky conditioning skin feel. The starch was also salt-sensitive causing it to "break" on the skin surface and rub in very well.

The above sample containing the CEPA modified potato starch and identified as Sample A was compared to control samples, Control-1 without the CEPA starch derivative and containing no thickener (Carbopol) or secondary emulsifier and Control-2 without the CEPA starch derivative but containing Carbopol and secondary emulsifiers. Also evaluated were two samples containing the CEPA potato starch, one without Carbopol (Sample B) and one without secondary emulsifiers (Sample C). The formulations are shown below:

|  | SAMPLES | | | | |
| --- | --- | --- | --- | --- | --- |
|  | A | B | C | CONTROL 1 | CONTROL 2 |
| PHASE A | | | | | |
| Cetyl Alcohol | 1.0 | 1.0 | 1.0 | 1.0 | 1.0 |
| Ceteth 20 | — | 1.0 | — | — | 1.0 |
| Glyceryl stearate SE | — | 1.0 | — | — | 1.0 |
| Octyl palmitate | 5.0 | 5.0 | 5.0 | 5.0 | 5.0 |
| $C_{12-15}$ alkyl benzoate | 5.0 | 5.0 | 5.0 | 5.0 | 5.0 |
| Stearic acid T.P. | 2.0 | 2.0 | 2.0 | 2.0 | 2.0 |
| Dimethicone copolyol | 1.0 | 1.0 | 1.0 | 1.0 | 1.0 |
| PHASE B | | | | | |
| Deionized water | 79.5 | 77.5 | 78.5 | 81.5 | 78.5 |
| Carbopol 940 | — | — | 0.5 | — | 0.5 |
| Triethanolamine (99%) | 0.5 | 0.5 | 1.0 | 0.5 | 1.0 |
| Propylene glycol | 3.0 | 3.0 | 3.0 | 3.0 | 3.0 |
| CEPA potato starch | 2.0 | 2.0 | 2.0 | — | — |
| PHASE C | | | | | |
| Germaben II E | 1.0 | 1.0 | 1.0 | 1.0 | 1.0 |

EXAMPLE II

The CEPA potato starch derivative described in Example I was formulated into a cosmetic lotion in the following manner:

An oil phase (Phase A) and water phase (Phase B) having the following ingredients were prepared and along with the preservative of Phase C, Germaben II E a product of Sutton Laboratories, which is a combination of propylene glycol (and) diazolidinyl urea (and) methylparaben and propylparaben, were combined and mixed to form a cosmetic lotion:

|  | PARTS BY WEIGHT |
| --- | --- |
| PHASE A | |
| Cetyl alcohol | 1.0 |
| Octyl palmitate | 5.0 |
| $C_{12-15}$ alkyl benzoate | 5.0 |
| Stearic acid T.P. | 2.0 |
| Dimethicone copolyol | 1.0 |
| PHASE B | |
| Deionized water | 79.5 |
| Triethanolamine (99%) | 0.5 |
| Propylene glycol | 3.0 |
| CEPA potato starch | 2.0 |
| PHASE C | |
| Germaben II E | 1.0 |

All of the above samples were placed in standard laboratory stability studies (one month)-ambient, oven (45° C.), freeze/thaw and refrigerator. Control 1 failed after 24 hours at 45° C., the emulsion splitting into phases. All other formulations passed the stability study. Aesthetically, sample formulation A, CEPA potato starch replacing Carbopol and without secondary emulsifiers had the best skin feel and appearance. This formulation had a very soft, conditioning, non-tacky feel and a nice white glossy look. Sample A and Control-2 were placed in accelerated viscosity studies at 45° C. and ambient temperature. Results are shown below:

|  |  | VISCOSITY cP | |
| --- | --- | --- | --- |
|  | TIME | SAMPLE A | CONTROL 2 |
| Ambient | Initial | 16,670 | 34,750 |
| 45° C. | Initial | 17,000 | 33,166 |
| Ambient | 1 week | 22,000 | 34,000 |
| 45° C. | 1 week | 17,500 | 17,583 |
| Ambient | 2 weeks | 22,500 | 34,644 |
| 45° C. | 2 weeks | 20,000 | 23,416 |
| Ambient | 8 weeks | 21,500 | 33,083 |
| 45° C. | 8 weeks | 13,000 | 27,500 |
| Ambient | 11 weeks | 22,000 | 32,166 |
| 45° C. | 11 weeks | 15,666 | 15,588 |
| Ambient | 20 weeks | 19,000 | 27,416 |
| 45° C. | 20 weeks | 11,083 (65%) | 7,083 (21%) |

The viscosity studies indicate that the CEPA potato starch Sample (A) is relatively stable over time and is actually superior to the Carbopol standard (Control 2). The CEPA potato starch sample maintained 65% of its viscosity at 45° C. while the Carbopol sample maintained only 21%.

EXAMPLE III

A moisturizing hand and body lotion containing the CEPA potato starch derivative described in Example I was formulated and had the following ingredients:

|  | Parts by Weight |
| --- | --- |
| Phase A | |
| N-butyl stearate | 8.00 |
| $C_{12-15}$ alkyl benzoate | 2.00 |
| Cetearyl octanoate | 5.00 |
| Isopropyl palmitate | 5.00 |
| Stearic acid T.P. | 2.00 |
| Cetyl alcohol | 1.00 |
| Lanolin alcohol | 0.50 |
| Dimethicone copolyol | 1.00 |
| Cyclomethicone | 3.00 |
| Phenyl trimethicone | 1.00 |
| Tocopherol acetate | 1.00 |
| Phase B | |
| Deionized water | 59.25 |
| Methylparaben | 0.15 |
| Propylparaben | 0.10 |
| Trisodium EDTA | 0.05 |
| Triethanolamine (99%) | 0.80 |
| Acrylates/octyl acrylamide copolymer | 1.00 |
| CEPA potato starch | 4.00 |
| Phase C | |
| Propylene glycol | 3.00 |
| Aluminum starch octenyl-succinate | 2.00 |
| Phase D | |
| Diazolidinyl urea | 0.15 |
|  | 100.00 |

The ingredients of Phase B except for the acrylate/acrylamide copolymer and aluminum starch octenyl-succinate were heated to 80° C. and the acrylate/acrylamide copolymer was slowly added with mixing until the addition was complete. The ingredients of Phase A were combined and heated to 80° C. and then added to Phase B while maintaining the temperature at 80° C. and mixing for 15 minutes. The mixture was then cooled to 40° C. Aluminum starch octenyl-succinate was slurried into propylene glycol and then added to the combined mixture at 40° C. and then Phase D was added and mixed until uniform. The formulation was then cooled to room temperature. This example shows the use of the CEPA potato starch derivative as a thickener and emulsion stabilizer.

EXAMPLE IV

A sunscreen composition containing an inorganic zinc oxide sun block and the CEPA potato starch derivative of Example I was formulated and had the following ingredients:

|  | Parts by Weight |
| --- | --- |
| Phase A | |
| Octyl methoxycinnamate | 7.50 |
| DEA cetyl phosphate | 1.50 |
| Cyclomethicone | 2.00 |
| Cetearyl alcohol | 1.00 |
| Tocopherol acetate | 0.50 |
| Cetearyl octanoate | 8.00 |
| Phase B | |
| Deionized water | 67.40 |
| Trisodium EDTA | 0.10 |
| Propylene glycol | 3.00 |
| CEPA potato starch | 2.00 |
| Phase C | |
| Zinc oxide | 6.00 |
| Phase D | |
| Germaben II E | 1.00 |
|  | 100.00 |

The ingredients of Phase B were combined with CEPA potato starch added slowly and then heated to 80° C. and mixed thoroughly. Phase A was combined and heated to 80° C. with mixing and then added to Phase B and mixed for 15 minutes. Then Phase C was added, mixed thoroughly and cooled to 40° C. followed by addition of Phase D with mixing. The CEPA starch derivative effectively viscosified a zinc oxide based system.

EXAMPLE V

A sunscreen composition (SPF 6) using an organic UV absorbing sunscreen was formulated and had the following ingredients:

|  | Parts by Weight |
| --- | --- |
| Phase A | |
| Octyl methoxycinnimate | 7.50 |
| Octyl palmitate | 5.00 |
| Cetyl alcohol | 1.00 |
| Stearic acid T.P. | 2.00 |
| Dimethicone copolyol | 1.00 |
| Phase B | |
| Deionized water | 80.60 |
| Methylparaben | 0.15 |
| Propylparaben | 0.10 |
| Triethanolamine (99%) | 0.50 |
| CEPA potato starch | 2.00 |
| Phase C | |
| Diazolidenyl urea | 0.15 |
|  | 100.00 |

The CEPA potato starch was added to Phase B ingredients and heated to 80° C. Phase A was combined, heated to 80° C. and then added to Phase B with mixing for 15 minutes. The mixture was cooled to 40° C., Phase C added and mixed thoroughly and the formulation then cooled to room temperature. This example illustrates a thickened, low surfactant containing sunscreen.

EXAMPLE VI

A shave cream composition containing the CEPA potato starch derivative of Example I was formulated with the following ingredients:

|  | Parts by Weight |
| --- | --- |
| Phase A |  |
| Stearic Acid T.P. | 8.00 |
| Phase B |  |
| Deionized water | 76.80 |
| Sodium lauryl sulfate | 7.00 |
| Triethanolamine (99%) | 5.00 |
| CEPA potato starch | 2.00 |
| Phase C |  |
| Germaben II E | 1.00 |
| [Propylene glycol (and) diazolidinyl urea (and) methylparaben (and) propylparaben] |  |
| Phase D |  |
| Fragrance | 0.20 |
|  | 100.00 |

The ingredients of Phase B were combined and heated to 80° C. In a separate vessel Phase A was heated to 80° C., then added to Phase B and mixed for 15 minutes. The mixture was cooled to 40° C., Phases C and D added with thorough mixing. After cooling to room temperature, the formulation was packaged in aerosol cans (96.5% concentrate of above formulation and 3.5% propellant A-46). This example illustrates the use of CEPA potato starch to effectively thicken a propellant based shave cream.

EXAMPLE VII

Another cosmetic composition, an after shave balm which contained the CEPA potato starch of Example I was formulated with the following ingredients:

|  | Parts by Weight |
| --- | --- |
| Phase A |  |
| N-butyl stearate | 4.00 |
| Cetyl palmitate | 2.50 |
| Myristyl propionate | 3.00 |
| Mineral Oil/PEG-30 Lanolin/Cetyl Alcohol | 1.50 |
| Phase B |  |
| Deionized water | 69.60 |
| Lecithin | 1.00 |
| CEPA potato starch | 2.00 |
| NaOH (25%) | 0.40 |
| Methylparaben | 0.15 |
| Propylparaben | 0.15 |

|  | Parts by Weight |
| --- | --- |
| Phase C |  |
| Glycerin | 7.00 |
| Aluminum starch octenyl succinate | 8.00 |
| Phenoxyethanol | 0.20 |
| Phase D |  |
| Fragrance | 0.50 |
|  | 100.00 |

The CEPA potato starch was dispersed in Phase B ingredients and heated to 80° C. Phase A ingredients were combined, heated to 80° C. and added to Phase B with mixing (15 minutes). After cooling to 40° C., aluminum starch octenyl succinate and glycerin were added followed by the addition of phenoxyethanol with thorough mixing. Phase D was added and the formulation mixed until uniform. This formulation represents an effectively thickened after shave balm emulsion.

EXAMPLE VIII

A cosmetic lotion for skin treatment containing alpha hydroxy acid and the CEPA potato starch of Example I was formulated with the following ingredients:

|  | Parts by Weight |
| --- | --- |
| Phase A |  |
| Isopropyl palmitate | 6.50 |
| Stearic acid T.P. | 4.00 |
| Glyceryl stearate | 2.00 |
| PEG 100 stearate | 2.00 |
| Cetyl alcohol | 1.50 |
| Isostearic acid | 1.00 |
| Dimethicone | 1.00 |
| PEG 40 stearate | 0.50 |
| Phase B |  |
| Deionized water | 68.55 |
| Ammonium hydroxide (28%) | 2.00 |
| CEPA potato starch | 2.00 |
| BHA | 0.10 |
| Sorbitan stearate | 0.50 |
| Phase C |  |
| Glycolic acid (70% solution) | 8.00 |
| Phase D |  |
| Immidazolidinyl urea | 0.35 |
|  | 100.00 |

Phase B ingredients were combined and heated to 80° C. Phase A ingredients were combined, heated to 80° C., added to Phase B and mixed for 15 minutes. After cooling to 50° C., Phase C was added with mixing and then Phase D added with thorough mixing. The formulation was cooled to room temperature and illustrates the use of CEPA potato starch to thicken a low pH, alpha hydroxy acid emulsion.

EXAMPLE IX

A liquid talc, solvent based cosmetic composition containing the CEPA potato starch of Example I was formulated with the following ingredients:

|  | Parts by Weight |
|---|---|
| Phase A | |
| Cetearyl alcohol | 0.50 |
| PPG 3 myristyl ether | 0.25 |
| Emulsifying wax N.F. | 2.50 |
| Phase B | |
| Deionized water | 64.50 |
| CEPA potato starch | 2.00 |
| Anhydrous ethanol | 20.00 |
| Polysorbate 80 (and) cetyl acetate (and) acetylate lanolin alcohol | 0.25 |
| Phase C | |
| Tapioca | 10.0 |
|  | 100.0 |

Deionized water and CEPA potato starch were combined, heated to 80° C., mixed for 10 minutes and after cooling to 60° C. the remaining Phase B ingredients were added. Phase A ingredients were combined, heated to 60° C. and added to Phase B with mixing. The mixture was cooled to 50° C., Phase C added with mixing and then cooled to room temperature. This formulation represents an effectively thickened solvent (ethanol) based system.

What is claimed is:

1. A cosmetic skin care or hair care composition comprising a cosmetic vehicle and from about 0.1 to about 20% by weight of an amino multicarboxylate starch derivative having the following structure:

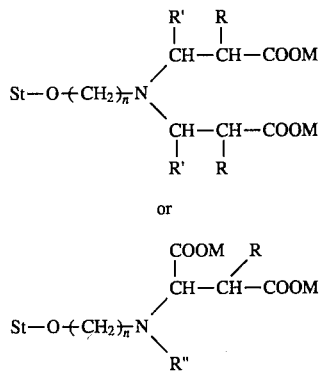

wherein

St-O represents a starch molecule;

R is H or $CH_3$;

R' is H, $CH_3$ or COOH;

M is a cation selected from the group consisting of hydrogen, alkali metal, alkaline earth metal and ammonium;

n is 2 or 3; and

R" is H or alkyl of 1 to 18 carbon atoms.

2. The composition of claim 1 wherein each R, R' and R" are H and M is H.

3. The composition of claim 2 wherein n is 2.

4. The composition of claim 3 wherein the starch derivative has the structure (I).

5. The composition of claim 4 wherein the starch is potato starch.

6. The composition of claim 4 wherein from about 0.3 to 5% by weight of the starch derivative is used based on the weight of the cosmetic composition.

7. The composition of claim 6 wherein the starch is potato starch.

8. The cosmetic composition of claim 1 wherein the cosmetic vehicle is an emulsion, an aqueous system, a solvent system or a mixture of aqueous and solvent systems.

9. The composition of claim 8 wherein the cosmetic vehicle comprises an emulsion of about 10 to 90% by weight of an oil phase and about 10 to 90% by weight of a water phase.

10. The composition of claim 9 wherein each R, R' and R" are H and M is H.

11. The composition of claim 10 wherein n is 2.

12. The composition of claim 11 wherein the starch derivative has the structure (I).

13. The composition of claim 12 wherein from about 0.1 to 20% by weight of the starch derivative is used based on the weight of the cosmetic composition.

14. The composition of claim 13 wherein the starch is potato starch.

15. The composition of claim 12 wherein 0.3 to 5% by weight of the starch derivative is used based on the weight of the cosmetic composition.

16. The composition of claim 15 wherein the starch is potato starch.

* * * * *